(12) United States Patent
Raft (10) Patent No.: US 11,838,718 B2
(45) Date of Patent: *Dec. 5, 2023

(54) HEARING PROTECTION DEVICE, HEARING PROTECTION SYSTEM, AND RELATED METHOD

(71) Applicant: GN Hearing A/S, Ballerup (DK)

(72) Inventor: Casper Silbo Raft, Ballerup (DK)

(73) Assignee: GN HEARING A/S, Ballerup (DK)

( * ) Notice: Subject to any disclaimer, the term of this patent is extended or adjusted under 35 U.S.C. 154(b) by 12 days.

This patent is subject to a terminal disclaimer.

(21) Appl. No.: 17/508,957

(22) Filed: Oct. 22, 2021

(65) Prior Publication Data

US 2022/0046353 A1 Feb. 10, 2022

Related U.S. Application Data

(63) Continuation of application No. 16/247,562, filed on Jan. 14, 2019, now Pat. No. 11,172,284.

(30) Foreign Application Priority Data

Jan. 24, 2018 (EP) .................................... 18153247

(51) Int. Cl.
*H04R 1/10* (2006.01)
*A61F 2/08* (2006.01)
(Continued)

(52) U.S. Cl.
CPC ............. *H04R 1/1083* (2013.01); *A61F 2/08* (2013.01); *A61F 11/06* (2013.01); *A61F 11/08* (2013.01); *H04R 1/1016* (2013.01); *A61F 11/145* (2022.01)

(58) Field of Classification Search
CPC ...... H04R 1/1083; H04R 1/1016; A61F 11/06
(Continued)

(56) References Cited

U.S. PATENT DOCUMENTS

| 7,352,871 B1 | 4/2008 | Mozo et al. |
| 9,216,113 B2 | 12/2015 | Harsch |

(Continued)

FOREIGN PATENT DOCUMENTS

| WO | WO 2005/029918 | 3/2005 |
| WO | WO 2005/029918 A1 | 3/2005 |

OTHER PUBLICATIONS

Final Office Action for U.S. Appl. No. 16/247,562 dated Jan. 28, 2021.

(Continued)

*Primary Examiner* — Disler Paul
(74) *Attorney, Agent, or Firm* — Vista IP Law Group, LLP (57) ABSTRACT

A hearing protection system, a hearing protection device and related method, the hearing protection device comprising an earpiece device comprising a first connector, and first and second earpieces, the first earpiece comprising a first primary microphone and a first receiver wired to the first connector and the second earpiece comprising a second primary microphone and a second receiver wired to the first connector; and a processing device comprising a processor, an earpiece interface, and a wireless communication interface, wherein the processor is configured to receive a first microphone input signal from the first primary microphone; process the first microphone input signal for provision of a first primary output signal for the first receiver based on the first microphone input signal; receive a communication request from a communication device via the communication interface; and in response to receipt of the communication request, communicate with the communication device via the communication interface.

31 Claims, 3 Drawing Sheets

(51) Int. Cl.
*A61F 11/06* (2006.01)
*A61F 11/08* (2006.01)
*A61F 11/14* (2006.01)

(58) Field of Classification Search
USPC .............................................. 381/77–82, 72
See application file for complete search history.

(56) References Cited

U.S. PATENT DOCUMENTS

| | | | |
|---|---|---|---|
| 9,613,611 B2 | 4/2017 | Ozluturk | |
| 9,958,275 B2* | 5/2018 | Chelian | H04B 1/385 |
| 10,111,014 B2 | 10/2018 | Schnell et al. | |
| 10,561,532 B2* | 2/2020 | Bui | H04R 1/1083 |
| 2011/0286608 A1 | 11/2011 | Hautier et al. | |
| 2012/0063622 A1* | 3/2012 | Bruckhoff | H04R 1/1016 |
| | | | 381/328 |
| 2014/0198926 A1 | 7/2014 | Killion et al. | |
| 2014/0270230 A1* | 9/2014 | Oishi | H04R 1/1041 |
| | | | 381/74 |
| 2015/0011259 A1 | 1/2015 | Chirde | |
| 2015/0131825 A1 | 5/2015 | Kim et al. | |
| 2016/0066093 A1* | 3/2016 | Fisher | H04R 5/04 |
| | | | 381/80 |

OTHER PUBLICATIONS

Final Office Action for U.S. Appl. No. 16/247,562 dated Feb. 28, 2020.
Non-Final Office Action for U.S. Appl. No. 16/247,562 dated Aug. 25, 2020.
Non-Final Office Action for U.S. Appl. No. 16/247,562 dated Jul. 12, 2019.
Amendment Response to NFOA for U.S. Appl. No. 16/247,562 dated Nov. 25, 2020.
Amendment Response to NFOA for U.S. Appl. No. 16/247,562 dated Jan. 10, 2020.
Amendment Response to FOA for U.S. Appl. No. 16/247,562 dated Mar. 29, 2021.
Notice of Allowance for U.S. Appl. No. 16/247,562 dated Jul. 13, 2021.
Communication pursuant to Article 94(3) dated Mar. 3, 2020 for corresponding European Application No. 18153247.4.
Foreign Office Action dated Apr. 2, 2022 for Chinese patent application No. 201910057584.9.
English translation of OA for Chinese Patent Application No. 201910057584.9 dated Apr. 2, 2022.

* cited by examiner

HEARING PROTECTION DEVICE, HEARING PROTECTION SYSTEM, AND RELATED METHOD

RELATED APPLICATION DATA

This application is a continuation of U.S. patent application Ser. No. 16/247,562 filed on Jan. 14, 2019, now U.S. Pat. No. 11,172,284, which claims priority to, and the benefit of, European Patent Application No. 18153247.4 filed on Jan. 24, 2018. The entire disclosures of the above applications are expressly incorporated by reference herein.

FIELD

The present disclosure relates to a hearing protection device, a hearing protection system comprising a hearing protection device and a communication device and related methods including a method of operating a hearing protection device.

BACKGROUND

In combat and/or emergency situations, it may be desirable for a user to protect his/her hearing while enabling the user to communicate with others via radio communication. Further, there is a desire to reduce the risk of malfunction and/or increase the wearing comfort of a hearing protection device for a user.

SUMMARY

Accordingly, there is a need for hearing protection devices, hearing protection systems and methods with improved wearing comfort for a user of the hearing protection device.

A hearing protection device is disclosed, the hearing protection device comprising an earpiece device comprising a first connector, a first earpiece, and a second earpiece, the first earpiece comprising a first primary microphone and a first receiver wired to the first connector and the second earpiece optionally comprising a second primary microphone and/or a second receiver optionally wired to the first connector or a second connector; and a processing device comprising a processor, an earpiece interface, and a wireless communication interface, wherein the processor is configured to receive a first microphone input signal from the first primary microphone; process the first microphone input signal for provision of a first primary output signal for the first receiver based on the first microphone input signal; receive a communication request from a communication device via the communication interface; and in response to receipt of the communication request, communicate with the communication device via the communication interface.

Also disclosed is a hearing protection system comprising a hearing protection device as described herein and a communication device configured for wireless communication with the hearing protection device.

Further, a method of operating a hearing protection device is disclosed, the hearing protection device comprising an earpiece device comprising a first connector, a first earpiece, and a second earpiece, the first earpiece comprising a first primary microphone and a first receiver wired to the first connector and the second earpiece optionally comprising a second primary microphone and/or a second receiver wired to the first connector; and a processing device comprising a processor, an earpiece interface, and a wireless communication interface, wherein the method comprises receiving a first microphone input signal from the first primary microphone; processing the first microphone input signal for provision of a first primary output signal for the first receiver based on the first microphone input signal; receiving a communication request from a communication device via the communication interface; and in response to receiving the communication request, communicating with the communication device via the communication interface.

Also disclosed is a communication device of a hearing protection system as described herein.

The present disclosure allows for improved wearing comfort for a user, by removing the need for a wired connection from the torso to the head or ears, in turn also reducing the risk of accidental removal of the earpieces, e.g. due to a tree branch catching the wire in a forest combat situation.

The present disclosure provides a power efficient hearing protection device with wireless communication.

A hearing protection device includes: an earpiece device comprising a first connector, a first earpiece, and a second earpiece, the first earpiece comprising a first primary microphone and a first receiver wired to the first connector, the second earpiece comprising a second primary microphone and a second receiver wired to the first connector; and a processing device comprising a processor, an earpiece interface, and a wireless communication interface; wherein the processor is configured to: receive a first microphone input signal from the first primary microphone; process the first microphone input signal for provision of a first primary output signal for the first receiver based on the first microphone input signal; receive a communication request from a communication device via the communication interface; and in response to the communication request, communicate with the communication device via the communication interface.

Optionally, the processor is configured to process the first microphone input signal by performing hear-through processing of the first microphone input signal.

Optionally, the processor comprises an impulse noise reduction module, and wherein the processor is configured to perform the hear-through processing of the first microphone input signal by applying impulse noise reduction to the first microphone input signal.

Optionally, the processor is configured to: receive a second microphone input signal from the second primary microphone; and process the second microphone input signal for provision of a second primary output signal for the second receiver based on the second microphone input signal.

Optionally, the processor is configured to process the second microphone input signal by performing hear-through processing of the second microphone input signal.

Optionally, the processor comprises an impulse noise reduction module, and wherein the processor is configured to perform the hear-through processing of the second microphone input signal by applying impulse noise reduction to the second microphone input signal.

Optionally, the communication request comprises a transmission request, and wherein the processor is configured to communicate with the communication device by transmitting an audio stream to the communication device via the communication interface in response to the transmission request.

Optionally, the communication request comprises a receive request, and wherein the processor is configured to communicate with the communication device by receiving an audio stream from the communication device via the communication interface in response to the receive request.

Optionally, the processing device is configured for attachment to a head worn device and/or an upper back portion of a body equipment.

Optionally, the hearing protection device further includes a first secondary microphone configured for picking up own voice of a user of the hearing protection device.

Optionally, the first earpiece comprises a first protection element for sealing an ear canal.

A hearing protection system includes the hearing protection device, and the communication device, wherein the communication device is configured for wireless communication with the hearing protection device.

Optionally, the communication device comprises a processor and an interface.

Optionally, the interface comprises one or more buttons.

Optionally, the interface comprises a radio interface for communication with a radio unit, and a hearing protection device interface for wireless communication with the hearing protection device.

A method of operating a hearing protection device comprising an earpiece device having a first connector, a first earpiece, and a second earpiece, the first earpiece comprising a first primary microphone and a first receiver wired to the first connector, the second earpiece comprising a second primary microphone and a second receiver wired to the first connector, wherein the hearing protection device further comprises a processing device comprising a processor, an earpiece interface, and a wireless communication interface, the method comprising: receiving a first microphone input signal from the first primary microphone; processing the first microphone input signal for provision of a first primary output signal for the first receiver based on the first microphone input signal; receiving a communication request from a communication device via the communication interface; and in response the communication request, communicating with the communication device via the communication interface.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

A hearing protection device is disclosed. The hearing protection system comprises a hearing protection device comprising a processing device and one or more earpieces including a first earpiece and/or a second earpiece. The processing device is optionally wired to the first earpiece and the second earpiece. The processing device may be configured for attachment to a head worn device, such as a helmet or other head protection device. The processing device may be configured for attachment to an upper back portion of a body equipment, such as a Molle vest. The processing device may be integrated in a helmet.

The hearing protection device comprises an earpiece device comprising a first connector, a first earpiece, and a second earpiece. An earpiece, such as first earpiece and/or second earpiece, comprises an earpiece housing. The earpiece housing may be configured for positioning in the ear of a user, such as in the concha and/or in the ear canal. The earpiece housing optionally comprises an ear canal portion and an outer ear portion. The ear canal portion extends along an ear canal axis, the ear canal portion having a first end. The first end of the ear canal portion points towards the eardrum of a user when the earpiece is inserted into the ear of a user. An ear canal opening may be arranged at the first end of the ear canal portion. The ear canal opening allows sounds to exit/enter the earpiece housing. A plurality of ear canal openings may be provided in the earpiece housing, e.g. to separate receiver sound and secondary (e.g. ear canal) microphone sound. The ear canal opening(s) of the earpiece may each have a diameter in the range from 0.5 mm to 3 mm. The same or different diameters may be applied for different ear canal openings. The ear canal portion may have a length (measured along the ear canal axis) in the range from 2 mm to 20 mm. In one or more exemplary earpieces, the ear canal portion has a length in the range from 3 mm to 15 mm. Thereby, the ear canal wall of the user can be used for fixating the earpiece in the ear canal and/or the ear canal can be sealed near the tympanic membrane on the inner surface of the ear canal. An earpiece is optionally configured as a hearing protector. Thus, the first earpiece may comprise a first protection element for sealing an ear canal. The second earpiece may comprise a second protection element for sealing an ear canal. A protection element, such as the first protection element and/or the second protection element, is configured for forming a seal between the ear canal wall and the ear canal portion of the earpiece (when inserted in the ear canal of the user). The protection element, such as the first protection element and/or the second protection element, may be made of or comprise foamed polymer. The protection element, such as the first protection element and/or the second protection element, may circumvent the ear canal portion. The protection element, such as the first protection element and/or the second protection element, may have a length (extension along the ear canal axis) of at least 2 mm, such as in the range from 5 mm to 20 mm. The protection element may be made of or comprise one or more of silicone gel, silicone foam, urethane gel, and urethane foam. The protection element may be made of or comprise one or more of liquid, foam, and air.

The first earpiece comprises a first primary microphone and a first receiver wired to the first connector. The hearing protection device, such as the first earpiece, may comprise a first secondary microphone configured for picking up own voice of a user of the hearing protection device. For example, the first secondary microphone may be configured as a first ear canal microphone and/or arranged in the first earpiece. An ear canal microphone is configured for picking up sound in the ear canal of a user. In one or more exemplary hearing protection devices, the first secondary microphone is arranged at the distal end of a boom. A proximal end of the boom may be attached to the first earpiece.

The second earpiece optionally comprises a second primary microphone and/or a second receiver wired to the first connector. The hearing protection device, such as the second earpiece, may comprise a second secondary microphone configured for picking up own voice of a user of the hearing protection device. For example, the second secondary microphone may be configured as a second ear canal microphone and/or arranged in the second earpiece. In one or more exemplary hearing protection devices, the second secondary microphone is arranged at the distal end of a boom. A proximal end of the boom may be attached to the second earpiece.

In the present disclosure, a primary microphone, such as the first primary microphone and/or the second primary microphone, is an external microphone configured to pick up external or ambient sounds.

A receiver, such as the first receiver and/or the second receiver, forms an audio signal based on an output signal. The output signal for the receiver may be a combination of one or more output signals, such as a combination or sum of a primary output signal and a secondary output signal.

The hearing protection device comprises a processing device comprising a processor, an earpiece interface, and a wireless communication interface. The earpiece interface comprises a connector for connecting the earpiece device to the processing device. The communication interface may comprise an antenna and a wireless transceiver, e.g. configured for wireless communication at frequencies in the range from 2.4 to 2.5 GHz. The communication interface may be configured for inductive coupling and communication with the communication device.

The hearing protection device is configured for wireless communication with the communication device. The hearing protection d induction communicate inductive coupling The processor of the processing device is configured to receive a first microphone input signal from the first primary microphone and process the first microphone input signal for provision of a first primary output signal forming at least a part of a first output signal for the first receiver based on the first microphone input signal. To process the first microphone input signal may comprise performing hear-through processing of the first microphone input signal. The processor may comprise an impulse noise reduction module. Performing hear-through processing of the first microphone input signal may comprise applying impulse noise reduction to the first microphone input signal. Thus, the hearing protection device may enable a user to hear ambient sounds, at least to a certain degree, e.g. allowing the user to hear other persons speak or react on ambient sounds, while providing hearing protection.

The processor of the processing device may be configured to receive a second microphone input signal from the second primary microphone and process the second microphone input signal for provision of a second primary output signal forming at least part of a second output signal for the second receiver based on the second microphone input signal. To process the second microphone input signal may comprise performing hear-through processing of the second microphone input signal. Performing hear-through processing of the second microphone input signal may comprise applying impulse noise reduction to the second microphone input signal. Thus, the hearing protection device may enable a user to hear ambient sounds, at least to a certain degree, e.g. allowing the user to hear other persons speak or react on ambient sounds, while providing hearing protection. A binaural hear-through processing may contribute to preserving binaural cues, e.g. to allow the user to locate an audio source, e.g. from which direction an audio signal is received.

Performing hear-through processing of the first microphone input signal may comprise applying noise reduction to the first microphone input signal. Performing hear-through processing of the second microphone input signal may comprise applying noise reduction to the second microphone input signal.

The processor of the processing device is configured to receive a communication request from a communication device via the communication interface, and in response to receipt of the communication request, communicate with the communication device via the communication interface. The processor of the processing device may be configured to receive a communication end request from the communication device via the communication interface, and in response to receipt of the communication end request, forgo to communicate with the communication device via the communication interface.

To receive the communication request may comprise to receive a transmission request and wherein to communicate with the communication device comprises transmitting an audio stream to the communication device via the communication interface in response to receiving the transmission request.

In one or more exemplary hearing protection devices, to communicate with the communication device in response to receiving the transmission request comprises to obtain a voice signal based on a first secondary microphone input signal from the first secondary microphone and/or based on a second secondary microphone input signal from the second secondary microphone and providing the audio stream based on the voice signal.

To receive the communication end request from the communication device via the communication interface may comprise to receive a transmission end request, and in response to receipt of the transmission end request, forgo transmitting the audio stream to the communication device.

To receive the communication request may comprise to receive a receive request and wherein to communicate with the communication device may comprise receiving an audio stream from the communication device via the communication interface in response to receiving the receive request.

In one or more exemplary hearing protection devices, to communicate with the communication device in response to receiving the receive request comprises to feed a first secondary output signal to the first receiver and/or a second secondary output signal to the second receiver based on the received audio stream.

To receive the communication end request from the communication device via the communication interface may comprise to receive a receive end request, and in response to receipt of the receive end request, forgo receiving the audio stream from the communication device.

The processor of the processing device may comprise a hear-through processing module for hear-through processing of the first microphone input signal and the second microphone input signal. The hear-through processing module may apply noise reduction, such as impulse noise reduction, to the first microphone input signal and outputs first primary output signal based on the first microphone input signal. The first primary output signal may be based on the first secondary microphone input signal. The hear-through processing module may apply noise reduction, such as impulse noise reduction, to the second microphone input signal and outputs second primary output signal based on at least the second microphone input signal. The second primary output signal may be based on the second secondary microphone input signal. The processor of the processing device may comprise an audio module. The audio module may comprise a voice module configured to form a voice signal based on one or more microphone input signals, such as the first secondary microphone input signal and/or the second secondary microphone input signal. The voice signal may be based on the first microphone input signal and/or the second microphone input signal. The voice signal may be based on the first output signal and/or the second output signal. The audio module may output the voice signal as audio output signal, e.g. in response to receipt of transmission request from communication device. The audio module may receive audio input signal from the communication interface. The audio module may be configured to form first secondary output signal and/or second secondary output signal based on the audio input signal. The processor of the processing device may comprise a mixing module configured to form first output signal based on first primary output signal and first secondary output signal. The mixing module may be configured to form second output signal based on second primary output signal and second secondary output signal. The first output signal may be a sum, such as a weighted sum, of the first primary output signal and the first secondary output signal. The second output signal may be a sum, such as a weighted sum, of the second primary output signal and the second secondary output signal.

The disclosed hearing protection system comprises a hearing protection device and a communication device configured for wireless communication with the hearing protection device. The communication device comprises a processor and an interface. The interface of the communication device comprises a user interface including one or more buttons, such as a first button; a radio interface for communication with a radio unit; and a hearing protection device interface for wireless communication with the hearing protection device. The first button may be configured as a push-to-talk button. The hearing protection device interface may comprise an antenna and a wireless transceiver, e.g. configured for wireless communication at frequencies in the range from 2.4 to 2.5 GHz. The hearing protection device interface may be configured for inductive coupling and communication with the hearing protection device.

The processor of the communication device may be configured to receive a user input indicative of own voice pickup and transmission via the user interface, e.g. by a user pressing and holding the first button; in response to the user input indicative of own voice pickup and transmission, transmitting a transmission request to the hearing protection device via the hearing protection device interface; receiving an audio stream from the hearing protection device, and outputting the audio stream via the radio interface. Outputting the audio stream via the radio interface may comprise outputting a push-to-talk control signal via the radio interface. The processor of the communication device may be configured to transmit a transmission end request, e.g. upon detection of user release of the first button.

The processor of the communication device may be configured to receive a control signal indicative of audio receipt via the radio interface; in response to the control signal indicative of audio receipt, transmitting a receive request to the hearing protection device via the hearing protection device interface; receiving an audio stream via the radio interface, and transmitting the audio stream to the hearing protection device via the hearing protection device interface. The processor of the communication device may be configured to detect absence of audio sent from the radio unit and in response to a detection of absence of audio sent from the radio unit, transmitting a receive end request to the hearing protection device via the hearing protection device interface.

The processor of the communication device may be configured to detect presence of an audio signal from the radio unit; in response to detecting an audio signal from the radio unit, transmitting a receive request to the hearing protection device via the hearing protection device interface; receiving an audio stream via the radio interface, and transmitting the audio stream to the hearing protection device via the hearing protection device interface.

The present disclosure relates to a method of operating a hearing protection device. In the method, receiving the communication request may comprise receiving a transmission request, and communicating with the communication device via the communication interface may comprise transmitting an audio stream in response to receiving the transmission request.

In the method, receiving the communication request may comprise receiving a receive request and communicating with the communication device via the communication interface may comprise receiving an audio stream from the communication device in response to receiving the receive request.

The method or at least parts thereof may be performed by a hearing protection system as disclosed herein.

Figure 1:
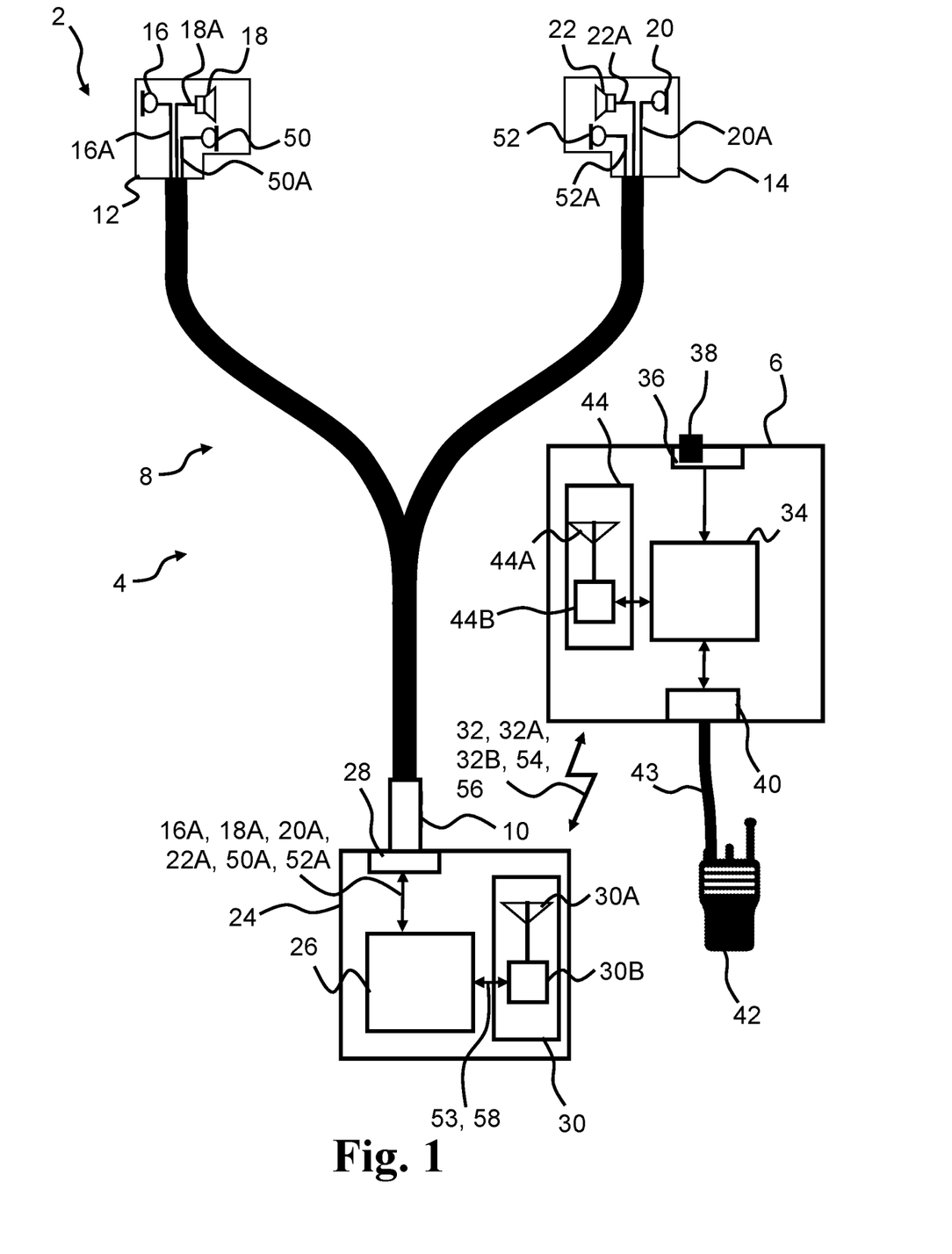
FIG. 1 schematically illustrates an exemplary hearing protection system according to the present disclosure.

FIG. 1 shows an exemplary hearing protection system. The hearing protection system 2 comprises a hearing protection device 4 and a communication device 6. The hearing protection device 4 comprises an earpiece device 8 comprising a first connector 10, a first earpiece 12, and a second earpiece 14, the first earpiece 12 comprising a first primary microphone 16 and a first receiver 18, both/each wired to the first connector 10. The second earpiece 14 comprises a second primary microphone 20 and a second receiver 22, both/each wired to the first connector 10 or a second connector. The hearing protection device 4 comprises a processing device 24 comprising a processor 26 such as a central processing unit (CPU) or a digital signal processor (DSP), an earpiece interface 28, and a wireless communication interface 30 comprising an antenna 30A and a transceiver 30B. The earpiece interface 28 comprises a first connector for forming a mechanical and electrical connection with the first connector of the earpiece device 8. The earpiece interface 28 may comprise a second connector for forming a mechanical and electrical connection with a second connector (not shown) of the earpiece device 8. The processor 26 is configured to receive a first microphone input signal 16A from the first primary microphone 16; process the first microphone input signal 16A including noise reduction, such as impulse noise reduction, for provision of a first primary output signal forming at least part of first output signal 18A for the first receiver 18 based on the first microphone input signal 16A; receive a communication request 32 from the communication device 6 via the communication interface 30; and in response to receipt of the communication request 32, communicate with the communication device 6 via the communication interface 30. Optionally, the processor 26 is configured to receive a second microphone input signal 20A from the second primary microphone 20; process the second microphone input signal 20A including noise reduction, such as impulse noise reduction, for provision of a second primary output signal forming at least part of second output signal 22A for the second receiver 22 based on the second microphone input signal 20A.

The communication device 6 comprises a processor 34 and an interface comprising a user interface 36 including one or more buttons, such as a first button 38; a radio interface 40 for connecting to and communicating with a radio unit 42 via connector cable 43; and a hearing protection device interface 44 for wireless communication with the hearing protection device 4.

The first earpiece 12 comprises a first secondary microphone 50 configured as a first ear canal microphone for picking up own voice of a user of the hearing protection device. A first secondary microphone input signal 50A from the first secondary microphone 50 is fed to processor 26 via earpiece interface 28. The second earpiece 14 optionally comprises a second secondary microphone 52 configured as a second ear canal microphone for picking up own voice of a user of the hearing protection device. A second secondary microphone input signal 52A from the second secondary microphone 52 is fed to processor 26 via earpiece interface 28.

The communication request 32 from the communication device 6 may comprise a transmission request 32A. The processor 26 is configured to, in response to receiving the transmission request 32A, obtain a voice signal, e.g. based on the first secondary microphone input signal 50A and/or the second secondary microphone input signal 52A, and provide an audio output signal 53 transmitted as an audio stream 54 based on the voice signal to the communication device 6 via the communication interface 30.

The communication request 32 from the communication device 6 may comprise a receive request 32B. The processor 26 is configured to, in response to receiving the receive request 32B, receiving an audio stream 56 from the communication device 6 via the communication interface 30. The audio stream 56 is converted to an audio input signal 58, and the processor 26 is configured to form first output signal 18A for the first receiver 18 and/or second output signal 22A for the second receiver based on the audio input signal 58 and/or microphone input signals 16A, 20A.

Turning to the communication device 6, the first button 38 may be configured as a push-to-talk button. In response to the user activating/pressing the first button 38, i.e. a user input indicative of own voice pickup and transmission, the communication device 6 transmits a transmission request 32A to the hearing protection device 4 via the hearing protection device interface 44; receives audio stream 54 from the hearing protection device (processing device 24), and outputs the audio stream via the radio interface 40 to the radio unit 42, wherein outputting the audio stream via the radio interface comprises outputting a push-to-talk control signal. When the user releases the first button, the processor 34 of the communication device may be configured to transmit a transmission end request to the hearing protection device.

Further, the processor 34 of the communication device may be configured to receive a control signal indicative of audio receipt via the radio interface 40; in response to the control signal indicative of audio receipt, transmitting a receive request 32B to the hearing protection device via the hearing protection device interface 44; receiving an audio stream via the radio interface, and transmitting the audio stream 56 to the hearing protection device via the hearing protection device interface 44. The processor of the communication device 6 may be configured to detect absence of audio sent from the radio unit 42 and in response to a detection of absence of audio sent from the radio unit, transmitting a receive end request to the hearing protection device via the hearing protection device interface.

Figure 2:
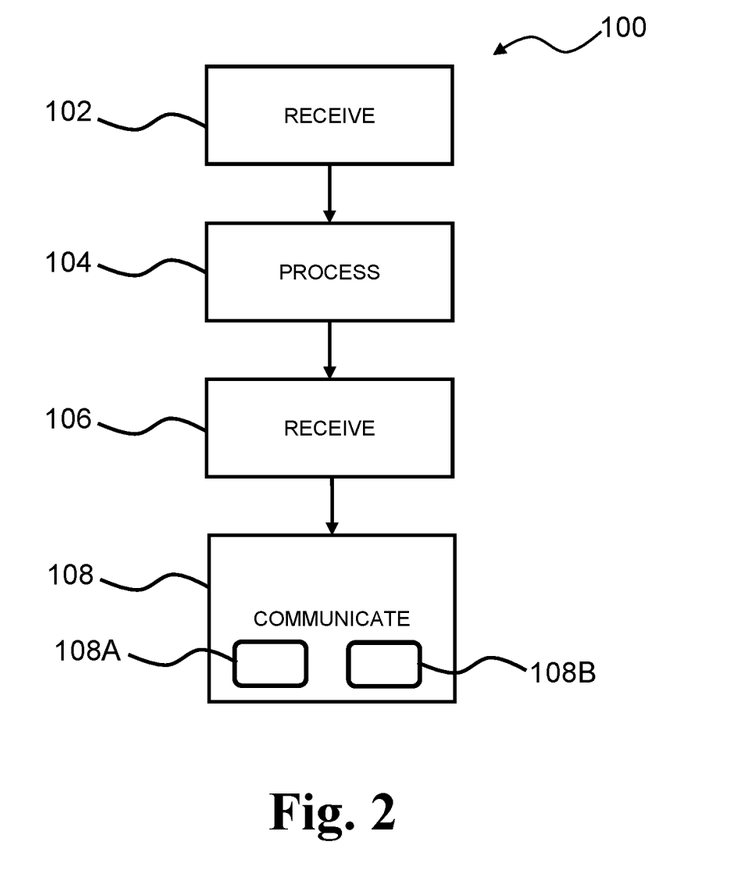
FIG. 2 is a flow diagram of an exemplary method according to the disclosure.

FIG. 2 is a flow diagram of an exemplary method of operating a hearing protection device comprising an earpiece device comprising a first connector, a first earpiece, and a second earpiece, the first earpiece comprising a first primary microphone and a first receiver wired to the first connector and the second earpiece comprising a second primary microphone and a second receiver wired to the first connector; and a processing device comprising a processor, an earpiece interface, and a wireless communication interface. The method 100 comprises receiving 102 a first microphone input signal from the first primary microphone;

processing 104 the first microphone input signal for provision of a first primary output signal for the first receiver based on the first microphone input signal;

receiving 106 a communication request from a communication device via the communication interface; and in response to receiving the communication request, communicating 108 with the communication device, i.e. receiving 108A and/or transmitting 108B audio streams from/to the communication device 6, via the communication interface.

Figure 3:
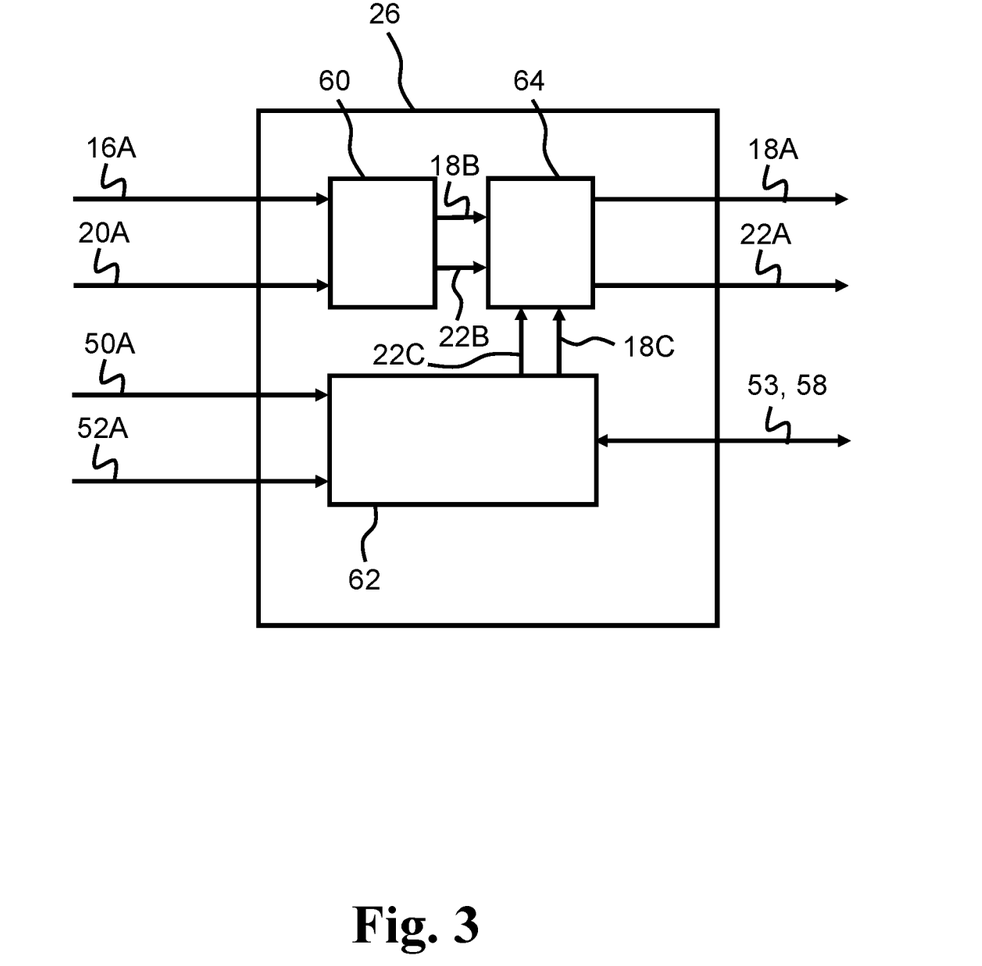
FIG. 3 is a block diagram of an exemplary processor of the processing device.

FIG. 3 is a schematic block diagram of a processor of the hearing protection device. The processor 26 comprises hear-through processing module 60 for hear-through processing of the first microphone input signal 16A and the second microphone input signal 20A. The hear-through processing module 60 applies noise reduction, such as impulse noise reduction, to the first microphone input signal 16A and outputs first primary output signal 18B based on the first microphone input signal 16A. The first primary output signal 18B may be based on the first secondary microphone input signal 50A. The hear-through processing module 60 applies noise reduction, such as impulse noise reduction, to the second microphone input signal 20A and outputs second primary output signal 22B based on at least the second microphone input signal 20A. The second primary output signal 22B may be based on the second secondary microphone input signal 52A. The processor 26 comprises an audio module 62. The audio module 62 comprises a voice module configured to form a voice signal based on the first secondary microphone input signal 50A and/or the second secondary microphone input signal 52A. The voice signal may be based on the first microphone input signal 16A and/or the second microphone input signal 20A (not shown). The voice signal may be based on the first output signal 18A and/or the second output signal 22A (not shown). The audio module 62 outputs the voice signal as audio output signal 53, e.g. in response to receipt of transmission request from communication device 6. The audio module 62 receives audio input signal 58 from the communication interface 30. The audio module 62 forms first secondary output signal 18C and second secondary output signal 22C based on the audio input signal 58. The processor 26 comprises a mixing module 64 configured to form first output signal 18A based on first primary output signal 18B and first secondary output signal 18C. The mixing module 64 is configured to form second output signal 22A based on second primary output signal 22B and second secondary output signal 22C. The first output signal 18A may be a sum, such as a weighted sum, of the first primary output signal 18B and the first secondary output signal 18C. The second output signal 22A may be a sum, such as a weighted sum, of the second primary output signal 22B and the second secondary output signal 22C.

LIST OF REFERENCES 2 hearing protection system
4 hearing protection device
6 communication device
8 earpiece device
10 first connector 10
12 first earpiece
14 second earpiece
16 first primary microphone
16A first microphone input signal
18 first receiver
18A first output signal
18B first primary output signal
18C first secondary output signal
20 second primary microphone
20A second microphone input signal
22 second receiver
22A second output signal
22B second primary output signal
22C second secondary output signal
24 processing device
26 processor
28 earpiece interface
30 wireless communication interface
30A antenna
30B transceiver
32 communication request
32A transmission request
32B receive request
34 processor
36 user interface
38 first button
40 radio interface
42 radio unit
43 connector cable
44 hearing protection device interface
44A antenna
44B transceiver
50 first secondary microphone
50A first secondary microphone input signal
52 second secondary microphone
52A second secondary microphone input signal
53 audio output signal
54 audio stream transmitted from processing device
56 audio stream from the communication device
58 audio input signal
60 hear-through processing module
62 audio module
64 mixing module
100 method of operating a hearing protection device
102 receiving a first microphone input signal from the first primary microphone
104 processing the first microphone input signal
106 receiving a communication request from a communication device
108 communicating with the communication device
108A receiving audio stream from the communication device
108B transmitting audio stream to the communication device

The invention claimed is:

1. A hearing protection device comprising:
   a first earpiece and a second earpiece for wear by a user, and a first connector, the first earpiece comprising a first primary microphone and a first receiver wired to the first connector, the second earpiece comprising a second primary microphone and a second receiver wired to the first connector or to a second connector; and
   a processing device comprising a processing unit, an earpiece interface, and a wireless communication interface;
   wherein the processing unit is configured to:
      receive a first microphone input signal from the first primary microphone;
      process the first microphone input signal for provision of a first primary output signal for the first receiver based on the first microphone input signal; and
      receive a first communication from a communication device of the user via the wireless communication interface; and
   wherein the processing device is configured to communicate with the communication device via the wireless communication interface after receiving the first communication;
   wherein the hearing protection device also comprises a first secondary microphone configured to pick up a voice of the user of the hearing protection device, and to provide a first microphone output, and wherein the wireless communication interface is configured to transmit an audio stream based on the first microphone output for reception by the communication device; and
   wherein the first communication is based on a presence of signal from a radio unit detected by the communication device.

2. The hearing protection device according to claim 1, wherein the processing unit is configured to apply an impulse noise reduction to the first microphone input signal to perform hear-through processing of the first microphone input signal.

3. The hearing protection device according to claim 2, wherein the processing unit comprises an impulse noise reduction module configured to apply the impulse noise reduction to the first microphone input signal.

4. The hearing protection device according to claim 1, wherein the processing unit is configured to:
   receive a second microphone input signal from the second primary microphone; and
   process the second microphone input signal for provision of a second primary output signal for the second receiver based on the second microphone input signal.

5. The hearing protection device according to claim 4, wherein the processing unit is configured to process the second microphone input signal by performing hear-through processing of the second microphone input signal.

6. The hearing protection device according to claim 5, wherein the processing unit is configured to perform the hear-through processing of the second microphone input signal by applying impulse noise reduction to the second microphone input signal.

7. The hearing protection device according to claim 1, wherein the first earpiece comprises a first protection element for sealing an ear canal.

8. A hearing protection system comprising the hearing protection device according to claim 1, and the communication device, wherein the communication device is configured for wireless communication with the hearing protection device.

9. The hearing protection system according to claim 8, wherein the communication device comprises a user interface configured to receive a user input from the user of the hearing protection device.

10. The hearing protection system according to claim 9, wherein the user interface of the communication device comprises one or more buttons.

11. The hearing protection system according to claim 9, wherein the communication device also comprises a radio interface for connection and communication with a radio unit via a cable, and a hearing protection device interface for wireless communication with the hearing protection device.

12. The hearing protection device according to claim 1, further comprising a second secondary microphone, wherein the first secondary microphone is a part of the first earpiece, and the second secondary microphone is a part of the second earpiece.

13. The hearing protection device according to claim 1, wherein the processing unit is configured to process the first microphone input signal by applying impulse noise reduction to the first microphone input signal.

14. The hearing protection device according to claim 1, wherein the first communication is provisioned by the communication device of the user in response to the user operating the communication device.

15. The hearing protection device according to claim 14, wherein the first communication is provisioned by a pressing of a user control at the communication device.

16. The hearing protection device according to claim 1, wherein the wireless communication interface is configured to transmit the audio stream based on the first microphone output provided by the first secondary microphone in response to the first communication.

17. The hearing protection device according to claim 1, wherein the first communication is provisioned by the communication device of the user in response to the communication device obtaining communication data.

18. The hearing protection device according to claim 1, wherein the first communication is configured to cause the wireless communication interface to receive audio data wirelessly from the communication device of the user.

19. The hearing protection device according to claim 1, wherein the processing device is configured for placement at a head-worn device or at a back of a body-gear.

20. The hearing protection device according to claim 19, wherein the head-worn device comprises a helmet, and the processing device is configured for attachment to the helmet.

21. A hearing protection device comprising:
a first earpiece and a second earpiece for wear by a user, and a first connector, the first earpiece comprising a first primary microphone and a first receiver wired to the first connector, the second earpiece comprising a second primary microphone and a second receiver wired to the first connector or to a second connector; and
a processing device comprising a processing unit, an earpiece interface, and a wireless communication interface;
wherein the processing unit is configured to:
receive a first microphone input signal from the first primary microphone;
process the first microphone input signal for provision of a first primary output signal for the first receiver based on the first microphone input signal; and
receive a first communication from a communication device of the user via the wireless communication interface; and
wherein the processing device is configured to communicate with the communication device via the wireless communication interface after receiving the first communication;
wherein the hearing protection device also comprises a first secondary microphone configured to pick up a voice of the user of the hearing protection device, and to provide a first microphone output, and wherein the wireless communication interface is configured to transmit an audio stream based on the first microphone output for reception by the communication device; and
wherein the first communication comprises a transmission request requesting the hearing protection device to perform signal transmission to the communication device via the wireless communication interface.

22. A hearing protection device comprising:
a first earpiece and a second earpiece for wear by a user, and a first connector, the first earpiece comprising a first primary microphone and a first receiver wired to the first connector, the second earpiece comprising a second primary microphone and a second receiver wired to the first connector or to a second connector; and
a processing device comprising a processing unit, an earpiece interface, and a wireless communication interface;
wherein the processing unit is configured to:
receive a first microphone input signal from the first primary microphone;
process the first microphone input signal for provision of a first primary output signal for the first receiver based on the first microphone input signal; and
receive a first communication from a communication device of the user via the wireless communication interface; and
wherein the processing device is configured to communicate with the communication device via the wireless communication interface after receiving the first communication;
wherein the hearing protection device also comprises a first secondary microphone configured to pick up a voice of the user of the hearing protection device, and to provide a first microphone output, and wherein the wireless communication interface is configured to transmit an audio stream based on the first microphone output for reception by the communication device; and
wherein the first communication comprises a receive request requesting the hearing protection device to perform signal reception from the communication device via the wireless communication interface.

23. A method performed by a hearing protection device comprising a first earpiece and a second earpiece for wear by the user, and a first connector, the first earpiece comprising a first primary microphone and a first receiver wired to the first connector, the second earpiece comprising a second primary microphone and a second receiver wired to the first connector or to a second connector, wherein the hearing protection device further comprises a processing device comprising a processing unit, an earpiece interface, and a wireless communication interface, wherein the method comprises:
receiving a first microphone input signal from the first primary microphone;
processing the first microphone input signal for provision of a first primary output signal for the first receiver based on the first microphone input signal;

receiving a first communication from a communication device of the user via the wireless communication interface; and communicating with the communication device via the wireless communication interface after the first communication is received;

wherein the method further comprises picking up a voice of the user of the hearing protection device by a first secondary microphone, and providing a first microphone output by the first secondary microphone, and wherein the act of communicating with the communication device comprises transmitting an audio stream based on the first microphone output by the wireless communication interface for reception by the communication device of the user;

wherein the first communication is based on a presence of signal from a radio unit detected by the communication device.

24. The method according to claim 23, further comprising:

receiving a second microphone input signal from the second primary microphone; and processing the second microphone input signal for provision of a second primary output signal for the second receiver based on the second microphone input signal.

25. The method according to claim 24, wherein the second microphone input signal is processed by performing hear-through processing of the second microphone input signal.

26. The method according to claim 25, wherein the hear-through processing of the second microphone input signal is performed by applying impulse noise reduction to the second microphone input signal.

27. The method according to claim 23, wherein the first earpiece comprises a first protection element for sealing an ear canal.

28. The method according to claim 23, further comprising providing a second microphone output by a second secondary microphone, wherein the first secondary microphone is a part of the first earpiece, and the second secondary microphone is a part of the second earpiece.

29. The method according to claim 23, wherein the act of processing the first microphone input signal comprises applying impulse noise reduction to the first microphone input signal.

30. A method performed by a hearing protection device comprising a first earpiece and a second earpiece for wear by the user, and a first connector, the first earpiece comprising a first primary microphone and a first receiver wired to the first connector, the second earpiece comprising a second primary microphone and a second receiver wired to the first connector or to a second connector, wherein the hearing protection device further comprises a processing device comprising a processing unit, an earpiece interface, and a wireless communication interface, wherein the method comprises:

receiving a first microphone input signal from the first primary microphone;

processing the first microphone input signal for provision of a first primary output signal for the first receiver based on the first microphone input signal;

receiving a first communication from a communication device of the user via the wireless communication interface; and communicating with the communication device via the wireless communication interface after the first communication is received;

wherein the method further comprises picking up a voice of the user of the hearing protection device by a first secondary microphone, and providing a first microphone output by the first secondary microphone, and wherein the act of communicating with the communication device comprises transmitting an audio stream based on the first microphone output by the wireless communication interface for reception by the communication device of the user;

wherein the first communication comprises a transmission request requesting the hearing protection device to perform signal transmission to the communication device via the wireless communication interface.

31. A method performed by a hearing protection device comprising a first earpiece and a second earpiece for wear by the user, and a first connector, the first earpiece comprising a first primary microphone and a first receiver wired to the first connector, the second earpiece comprising a second primary microphone and a second receiver wired to the first connector or to a second connector, wherein the hearing protection device further comprises a processing device comprising a processing unit, an earpiece interface, and a wireless communication interface, wherein the method comprises:

receiving a first microphone input signal from the first primary microphone;

processing the first microphone input signal for provision of a first primary output signal for the first receiver based on the first microphone input signal;

receiving a first communication from a communication device of the user via the wireless communication interface; and communicating with the communication device via the wireless communication interface after the first communication is received;

wherein the method further comprises picking up a voice of the user of the hearing protection device by a first secondary microphone, and providing a first microphone output by the first secondary microphone, and wherein the act of communicating with the communication device comprises transmitting an audio stream based on the first microphone output by the wireless communication interface for reception by the communication device of the user;

wherein the first communication comprises a receive request requesting the hearing protection device to perform signal reception from the communication device via the wireless communication interface.

\* \* \* \* \*